(12) United States Patent
Schleich

(10) Patent No.: US 8,412,343 B2
(45) Date of Patent: Apr. 2, 2013

(54) CHANNEL SPECIFIC GAIN CONTROL INCLUDING LATERAL SUPPRESSION

(75) Inventor: Peter Schleich, Vill (AT)

(73) Assignee: Med-El Elektromedizinische Geraete GmbH, Innsbruck (AT)

( * ) Notice: Subject to any disclaimer, the term of this patent is extended or adjusted under 35 U.S.C. 154(b) by 469 days.

(21) Appl. No.: 12/695,240

(22) Filed: Jan. 28, 2010

(65) Prior Publication Data

US 2010/0191309 A1    Jul. 29, 2010

Related U.S. Application Data

(60) Provisional application No. 61/147,855, filed on Jan. 28, 2009.

(51) Int. Cl.
*A61N 1/08* (2006.01)
(52) U.S. Cl. .......................................................... 607/57
(58) Field of Classification Search ............... 607/55, 607/56, 57
See application file for complete search history.

(56) References Cited

U.S. PATENT DOCUMENTS

| | | | |
|---|---|---|---|
| 4,284,856 A | 8/1981 | Hochmair et al. | 179/107 E |
| 4,428,377 A | 1/1984 | Zollner et al. | 128/419 |
| 4,515,158 A | 5/1985 | Patrick et al. | 128/419 R |
| 5,215,085 A | 6/1993 | Von Wallenberg-Pachaly | 128/420.6 |
| 5,601,617 A | 2/1997 | Loeb et al. | 607/56 |
| 5,749,912 A | 5/1998 | Zhang et al. | 607/57 |
| 5,938,691 A | 8/1999 | Schulman et al. | 607/57 |
| 6,175,767 B1 | 1/2001 | Doyle, Sr. | 607/57 |
| 6,219,580 B1 | 4/2001 | Faltys et al. | 607/57 |
| 6,289,247 B1 | 9/2001 | Faltys et al. | 607/57 |
| 6,295,472 B1 | 9/2001 | Rubinstein et al. | 607/55 |
| 6,584,525 B1 | 6/2003 | Klingman | 710/118 |
| 6,594,525 B1 | 7/2003 | Zierhofer | 607/57 |
| 6,600,955 B1 | 7/2003 | Zierhofer | 607/57 |

(Continued)

FOREIGN PATENT DOCUMENTS

| | | |
|---|---|---|
| WO | WO 99/35882 | 7/1999 |
| WO | WO 99/49815 | 10/1999 |

(Continued)

OTHER PUBLICATIONS

Kral, A., et al, "Spatial resolution of cochlear implants: the electrical field and excitation of auditory afferents", *Hearing Research*, vol. 121 (1998, pp. 11-28.

(Continued)

*Primary Examiner* — Niketa Patel
*Assistant Examiner* — Alyssa M Alter
(74) *Attorney, Agent, or Firm* — Sunstein Kann Murphy & Timbers LLP

(57) ABSTRACT

A method is described for generating electrode stimulation signals for a plurality of stimulation electrodes in an implanted electrode array. An acoustic audio signal is processed with a bank of filters to generate a set of band pass signals where each band pass signal corresponds to a band of audio frequencies associated with one of the filters. A lateral suppression network is used to perform channel specific dynamic amplitude mapping of the band pass signals to generate a set of compressed band pass signals. Stimulation information is extracted from the compressed band pass signals to generate a set of stimulation timing signals, and the stimulation timing signals are developed into a set of electrode stimulation signals to the stimulation electrodes.

17 Claims, 7 Drawing Sheets

U.S. PATENT DOCUMENTS

| | | | |
|---|---|---|---|
| 6,731,767 B1 | 5/2004 | Blamey et al. | 381/312 |
| 6,778,858 B1 | 8/2004 | Peeters | 607/57 |
| 6,826,430 B2 | 11/2004 | Faltys et al. | 607/137 |
| 7,136,706 B1 | 11/2006 | Voelkel | 607/57 |
| 7,209,789 B2 | 4/2007 | Zierhofer | 607/57 |
| 7,242,985 B1 * | 7/2007 | Fridman et al. | 607/56 |
| 7,305,100 B2 | 12/2007 | Pedersen | 381/320 |
| 2001/0031909 A1 | 10/2001 | Faltys et al. | 600/25 |
| 2004/0082985 A1 | 4/2004 | Faltys et al. | 607/116 |
| 2004/0136545 A1 | 7/2004 | Sarpeshkar et al. | 381/98 |
| 2005/0107843 A1 | 5/2005 | McDermott et al. | 607/57 |
| 2005/0203589 A1 | 9/2005 | Zierhofer | 607/57 |
| 2006/0052841 A1 | 3/2006 | Daly et al. | 607/57 |
| 2006/0080087 A1 | 4/2006 | Vandali et al. | 704/207 |
| 2006/0227986 A1 | 10/2006 | Swanson et al. | 381/312 |
| 2006/0265061 A1 | 11/2006 | Kwon et al. | 623/10 |
| 2007/0156202 A1 | 7/2007 | Zierhofer | 607/57 |
| 2007/0225776 A1 | 9/2007 | Fritsch et al. | 607/57 |
| 2009/0024185 A1 | 1/2009 | Kulkarni et al. | 607/57 |

FOREIGN PATENT DOCUMENTS

| | | |
|---|---|---|
| WO | WO 01/19135 | 3/2001 |
| WO | WO 01/19304 | 3/2001 |
| WO | WO 2005/113064 | 12/2005 |
| WO | WO 2006/119069 | 11/2006 |

OTHER PUBLICATIONS

Loizou, P.C., "Signal Processing for Cochlear Prosthesis: A Tutorial Review", *IEEE*, Jan. 1997, pp. 881-885; 0-7803-3694.

Loizou, P.C., "Signal-Processing Techniques for Cochlear Implants", *IEEE Engineering in Medicine and Biology*, May/Jun. 1999, pp. 34-46.

McKay, Colette, et al, "The effect of rate of stimulation on perception of spectral shape by cochlear implantees", *Journal of Acoustical Society of America*, AIP/Acoustical Society of America, Melville, NY, US, vol. 118; No. 1; Jan. 1, 2005, pp. 386-392; XP012073185; ISSN: 001-4966.

Secker-Walker, H., et al, "Time-domain analysis of auditory-nerve-fiber firing rates", *J. Acoust. Soc. Am.* 88(3), pp. 1427-1436 (1990).

Wilson, B.S., et al, "Comparative Studies of Speech Processing Strategies for Cochlear Implants", *Laryngoscope*, vol. 96, No. 10, pp. 1068-1077, Oct. 1988.

Wilson, B. S., et al, "Better speech recognition with cochlear implants", *Nature*, vol. 352, pp. 236-238, Jul. 18, 1991.

Wilson, B. S., et al, "Seventh Quarterly Progress Report; Speech Processors for Auditory Prostheses", *Center for Auditory Prosthesis Research*, pp. 1-69, 1994.

Wilson, B. S., et al, "Temporal Representations With Cochlear Implants", *The American Journal of Otology*, 18:530-534, 1997.

Ziese, M., et al, "Speech Understanding with the CIS and the n-of-m Strategy in the MED-EL COMBI 40+ System", *ORL*, 2000;62:321-329.

European Patent Office, International Search Report, PCT/US2010/022311, Apr. 16, 2010.

Grayden, et al, "A Cochlear Implant Speech Processing Strategy Based on an Auditory Model", *Proceedings of the 2004 Intelligent Sensors Sensors Networks and Information Processing Conference*, Dec. 14-17, 2004; pp. 491-496.

Sit., J., et al, "A Low-Power Asynchronous Interleaved Sampling Algorithm for Cochlear Implants that Endoes Enelope and Phase Information", *IEEE Trans Biomed Eng.*, Jan. 2007; 54(1), pp. 138-149.

Vandali, A., et al, "Pitch ranking ability of cochlear implant recipients: A comparison of sound-processing strategies", *Accoust Soc. Am.*, May 2005; 117(5); pp. 3126-3138.

* cited by examiner

CHANNEL SPECIFIC GAIN CONTROL INCLUDING LATERAL SUPPRESSION

This application claims priority from U.S. Provisional Application 61/147,855, filed Jan. 28, 2009, which is incorporated herein by reference.

FIELD OF THE INVENTION

The present invention relates to medical implants, and more specifically to signal processing for cochlear implant systems.

BACKGROUND ART

In a cochlear implant (CI) the amplitude of the acoustic audio signal has to be mapped to a relatively small dynamic range which can be delivered to the acoustic nerve. Typically two stages perform this amplitude compression, a front-end automatic gain control (AGC) which controls the overall loudness and an instantaneous non-linear mapping function of typically logarithmic shape which further compresses each band-pass envelope. The dynamic AGC used in current CI systems usually applies one gain to the entire analyzed frequency range before splitting the acoustic audio signal into individual frequency bands. Such systems have been shown to increase listening comfort and speech understanding in hearing aid (HA) users as well as CI users.

One possible drawback of such a system can occur in the presence of two signals which are located in different frequency regions, such as a speech signal in the presence of a continuous high frequency noise. In such an acoustic environment, the AGC gain would depend on the relative amplitudes of the two signals. Assuming a loud high frequency noise, the AGC gain would be reduced by the noise signal which could result in suppression of the speech signal. In a unilaterally implanted patient, this might only result in reduced speech understanding. But in bilaterally implanted patients, there could also be a reduced ability to localize sound sources. For example, assuming the loud high frequency noise source is located at the right side of the CI user, then the right-side AGC would reduce its gain more than the left-side AGC. Consequently, the interaural level differences at high frequencies would be reduced, and since the acoustic head shadow effect is higher at high frequencies, the interaural level difference at low frequency could vanish or even be inverted. As a result, the low frequency components, for example originating from a car engine, would be perceived from the wrong side.

These undesirable side effects of front-end single channel signal compression could generally be circumvented by using AGCs which compress individual band pass signals instead of the broadband signal. Such solutions can be found both in hearing aids and in cochlear implant systems. Speech understanding in the presence of noise sounds and sound localization in bilateral patients could potentially be enhanced. One major drawback of such systems is the fact that spectral differences such as amplitude differences in adjacent analysis bands get reduced. Spectral information such as formant frequencies in speech signals could also be less accessible to HA and CI users.

There have been previous efforts to apply dynamic compression to band pass signals. For example, FIG. 1 shows an arrangement described in U.S. Pat. No. 7,136,706 (incorporated herein by reference) which applies an overall mapping to a pre-band pass signal and then band specific mapping. The pre-band pass mapping function is thought to be linear (i.e. a limiter). The post-band pass mapping function is implemented as a non-linear, compressive, or logarithmic transform. The inventors state that the differences in acoustic spectrum component amplitudes are maintained. By maintaining these differences, spectral smearing between channels is reduced and speech cues are preserved. But dynamic adaptation of post-band pass compression would result in unwanted spectral smearing.

A second method which applies frequency specific gains is described in U.S. Pat. No. 6,731,767 (incorporated herein by reference). As shown in the block diagram in FIG. 2, an acoustic audio signal is split into a number of separate frequency bands and variable gain is applied to each frequency band independently. In contrast to previously used AGC circuits, the gain is controlled by a gain comparator and statistical estimates of each band pass signal are calculated and compared to predetermined hearing response parameters. Although the gain calculation appears to be dynamic in this patent, it does not describe any interaction between analysis channels.

U.S. Pat. No. 7,305,100 describes a dynamic compression process which applies channel specific gains for use in a hearing aid, although no mention is found of use in a cochlear implant system. Although as shown in FIG. 3, there is a gain control unit, no details are discussed with regards to interactions between the analysis frequency bands.

U.S. Patent Publication 2004/0136545 describes an arrangement for distributed gain control which takes into account the interactions between analysis channels. FIG. 4 shows a block diagram of the arrangement discussed which is described as providing a spectral enhancement system that includes distributed filters, energy distribution units, and a weighted-averaging unit. Instead of filter banks as used in cochlear implants and hearing aids, a filter cascade is used with an energy-detector that is coupled to each filter and provides an energy-detection output signal. A weighted-averaging unit provides a weighted-averaging signal to each of the filters and distributed gain is applied to the filter stages via a nonlinear function.

SUMMARY OF THE INVENTION

Embodiments of the present invention are directed to generating electrode stimulation signals for a plurality of stimulation electrodes in an implanted electrode array. An acoustic audio signal is processed with a bank of filters to generate a set of band pass signals where each band pass signal corresponds to a band of audio frequencies associated with one of the filters. A lateral suppression network is used to perform channel specific dynamic amplitude mapping of the band pass signals to generate a set of compressed band pass signals. Stimulation information is extracted from the compressed band pass signals to generate a set of stimulation timing signals, and the stimulation timing signals are developed into a set of electrode stimulation signals to the stimulation electrodes.

The lateral suppression network may be based on automatic gain control circuitry using a multiplication matrix, in which case matrix elements along a main diagonal may have a lower value than adjacent matrix elements. For example, matrix elements along the main diagonal may have a value of zero. The lateral suppression network may allow individual lateral decay of suppression. The lateral suppression network may weight one or more of the band pass signals to be independent of the other band pass signals and/or to be influenced by spatially adjacent band pass signals. The weighted band pass signals may be averaged with the spatially adjacent band pass signals. The lateral suppression network may laterally suppress the one or more band pass signals when a spatially adjacent band pass signal has a higher amplitude.

Embodiments of the present invention include a computer program product implemented in a computer readable storage medium for generating electrode stimulation signals for a plurality of stimulation electrodes in an implanted electrode array according to any of the above. Embodiments also include a cochlear implant system operating according to any of the above.

DETAILED DESCRIPTION OF SPECIFIC EMBODIMENTS

Various embodiments of the present invention are directed to extending cochlear implant signal processing with an additional signal processing block that calculates channel specific dynamic amplitude mapping with gain suppression. Such an approach can enhance spectral details and model masking effects as known from normal hearing psychoacoustics. In addition, channel specific interaural level differences can be preserved in patients with bilateral cochlear implants.

Figure 1:
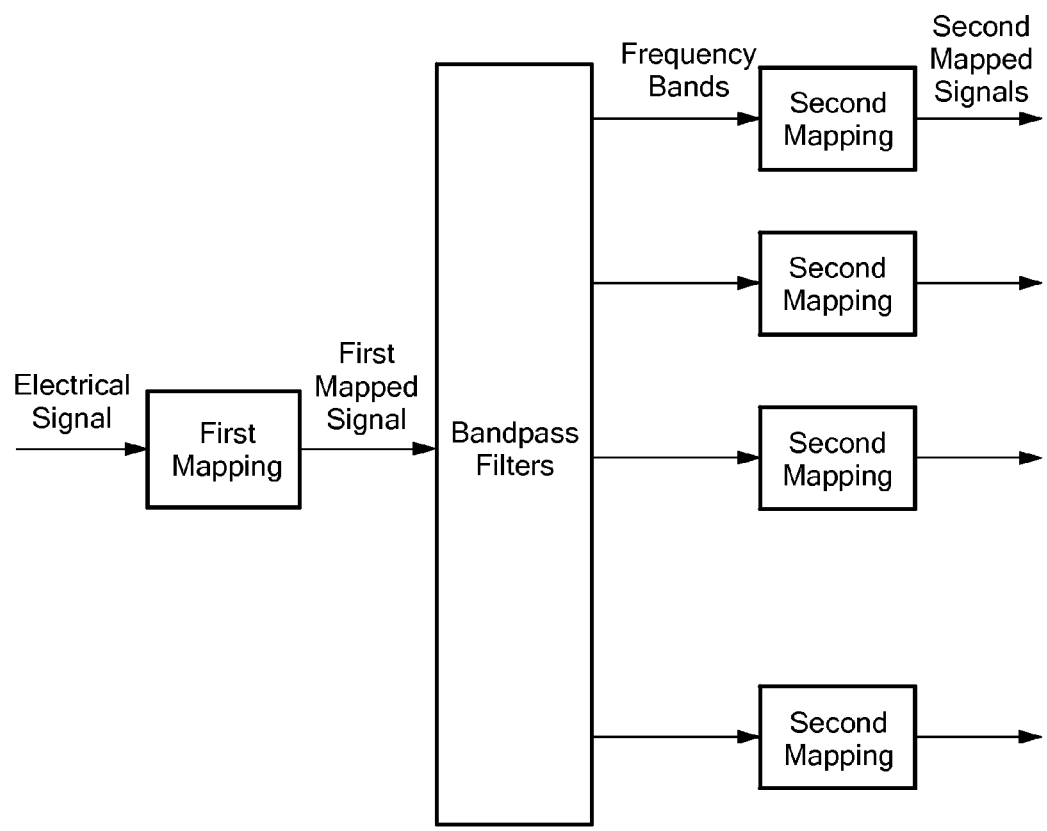
FIG. 1 shows a typical prior art cochlear implant signal compression arrangement.
Figure 2:
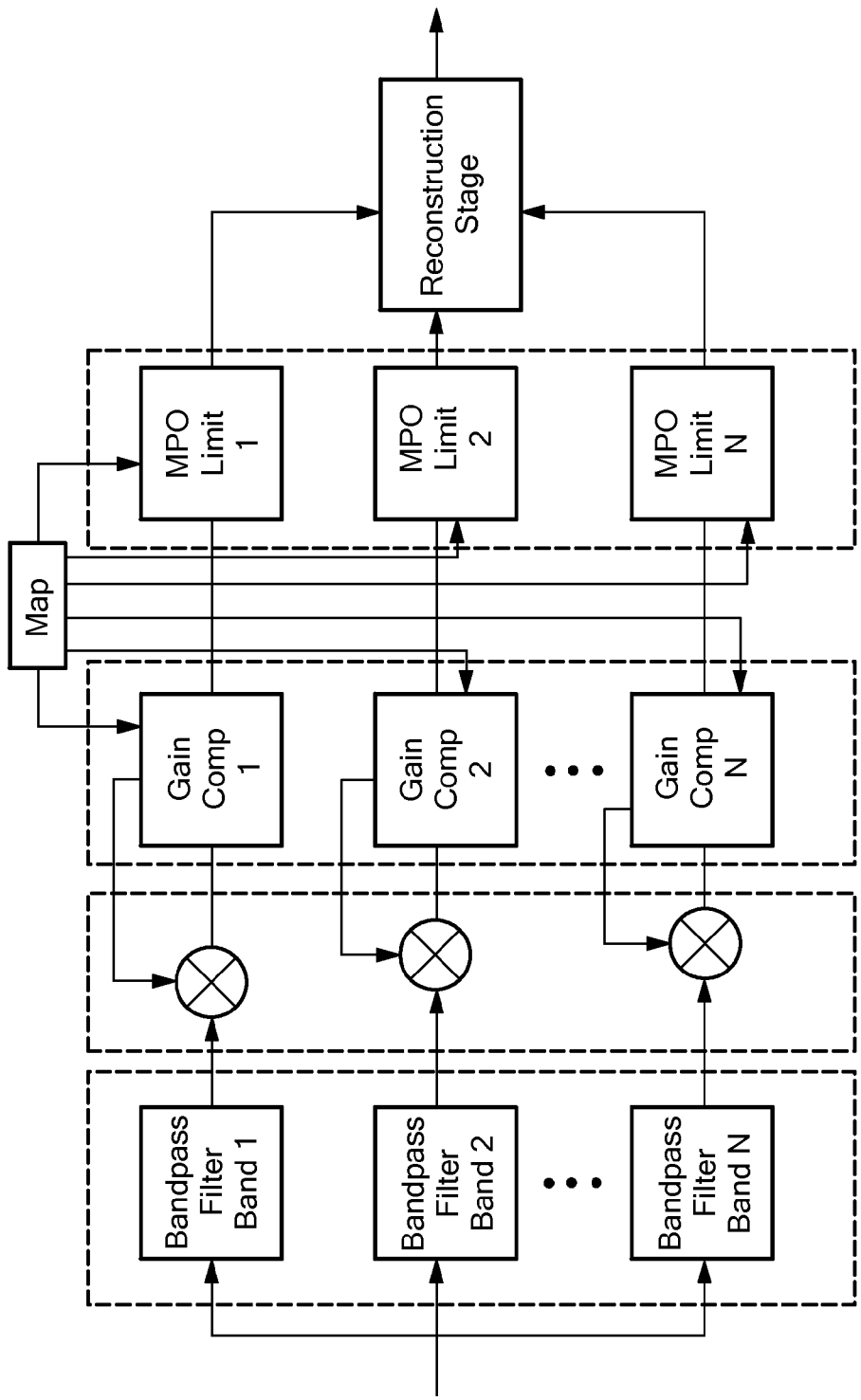
FIG. 2 shows a prior art signal compression arrangement having independent channels.
Figure 3:
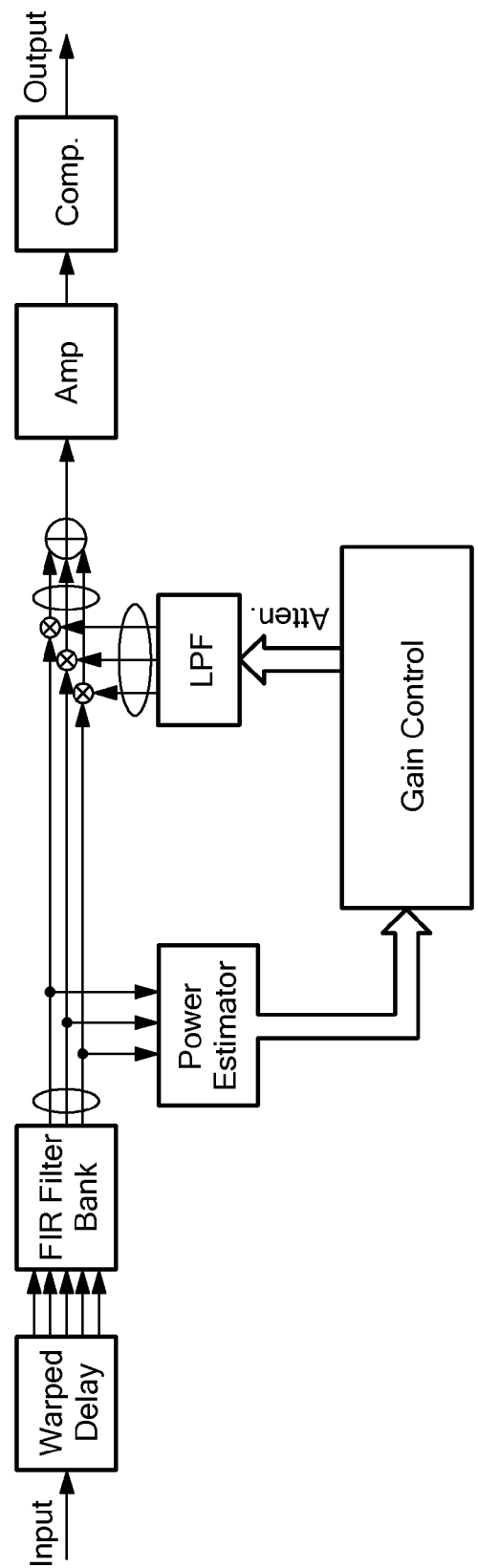
FIG. 3 shows a prior art signal compression arrangement having non-interactive channel specific gains.
Figure 4:
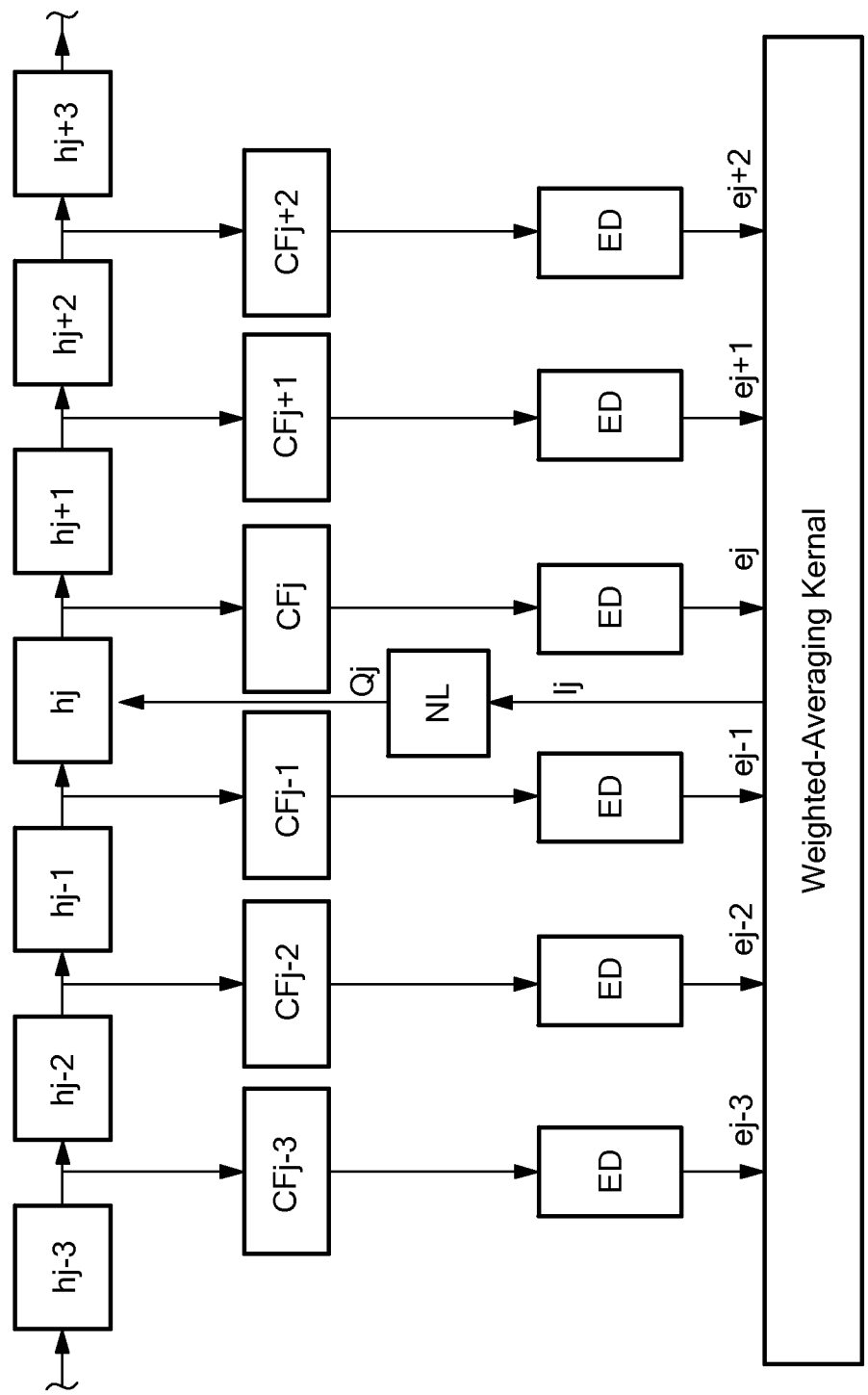
FIG. 4 shows a prior art signal compression system based on a filter cascade arrangement.
Figure 5:
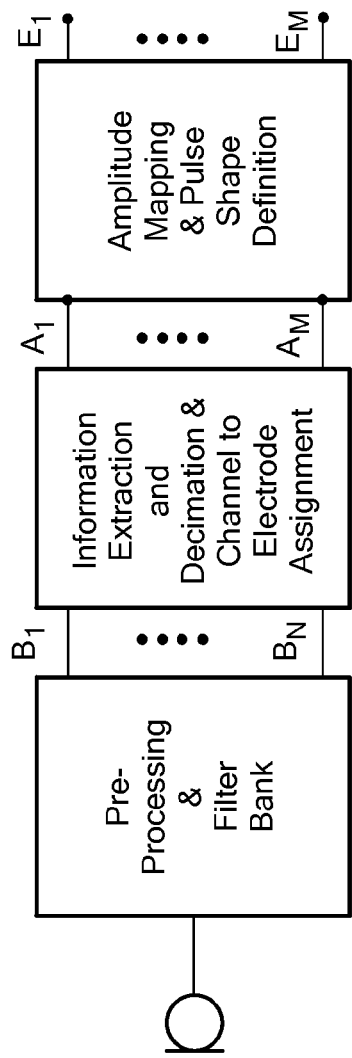
FIG. 5 shows a block diagram of a typical cochlear implant signal processing arrangement.

FIG. 5 shows various function blocks in a typical cochlear implant signal processing arrangement for generating electrode stimulation signals for the stimulation electrodes in an implanted electrode array. An acoustic audio signal from a sensing microphone is initially pre-processed such as by an initial AGC, a limiter, and/or noise reduction means, and then split by a filter bank into a set of band pass signals $B_n$ where each band pass signal corresponds to a band of audio frequencies associated with one of the filters. A set of stimulation timing signals $A_m$ are derived or determined which in effect maps the filter analysis frequency bands to the stimulation electrodes. From these, a set of patient mapping and stimulation pulses $E_m$ are defined.

Figure 6:
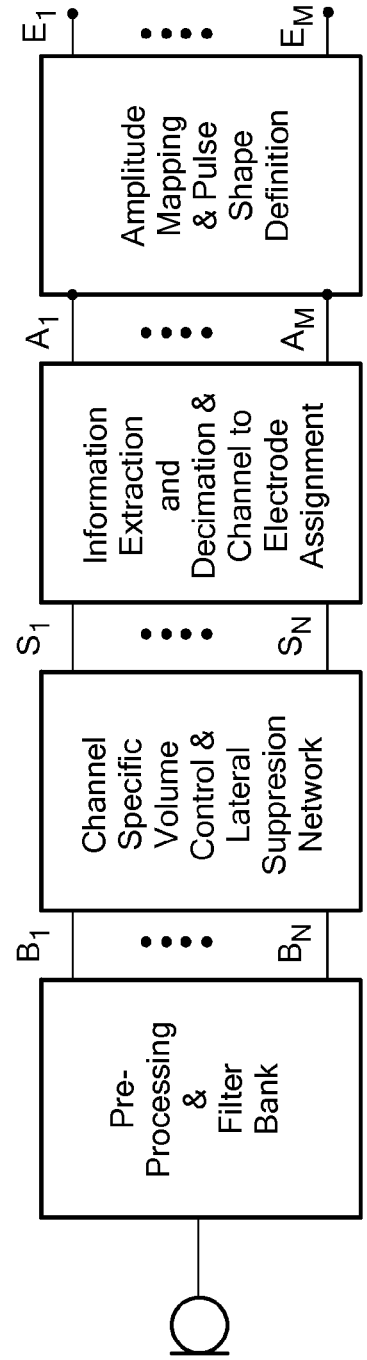
FIG. 6 shows a block diagram for a cochlear implant signal processing arrangement including channel specific volume control according to an embodiment of the present invention.

FIG. 6 shows functional blocks according to an embodiment of the present invention where a lateral suppression network is used to perform channel specific dynamic amplitude mapping of the band pass signals to generate a set of compressed band pass signals $S_n$. Stimulation information is extracted from the compressed band pass signals to generate a set of stimulation timing signals $A_m$, and the stimulation timing signals are developed into a set of electrode stimulation signals $E_m$ to the stimulation electrodes.

Figure 7:
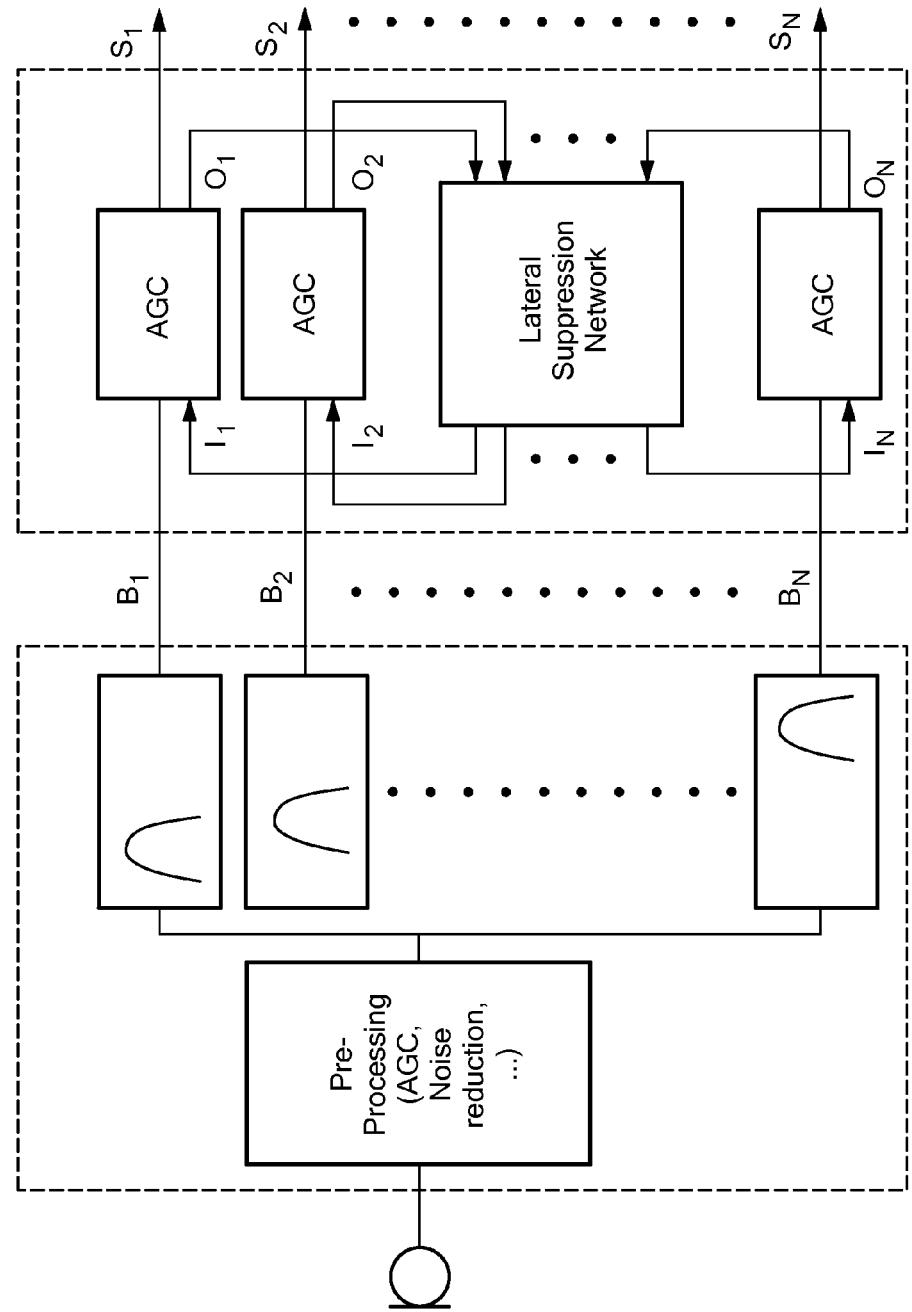
FIG. 7 shows further details of a channel specific volume control arrangement with a lateral suppression network.
Figure 8:
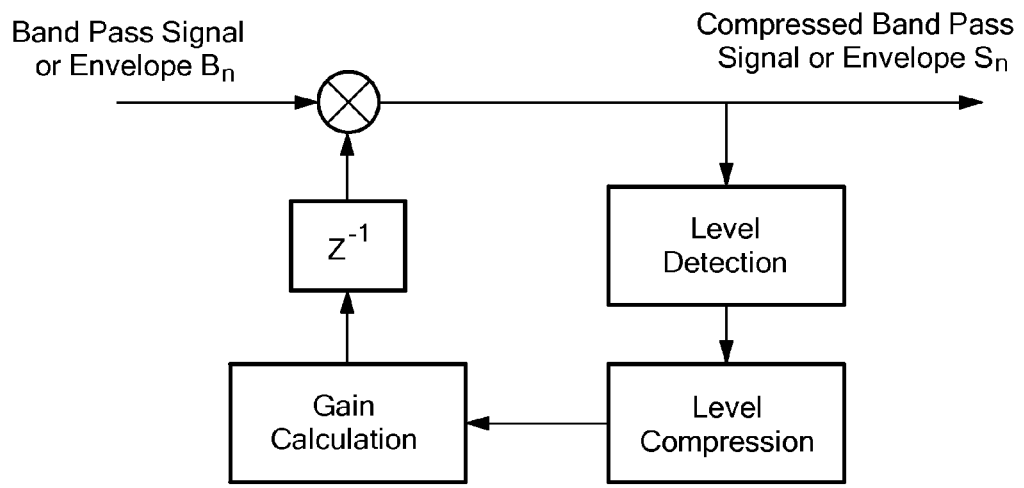
FIG. 8 shows functional details of an AGC arrangement.
Figure 9:
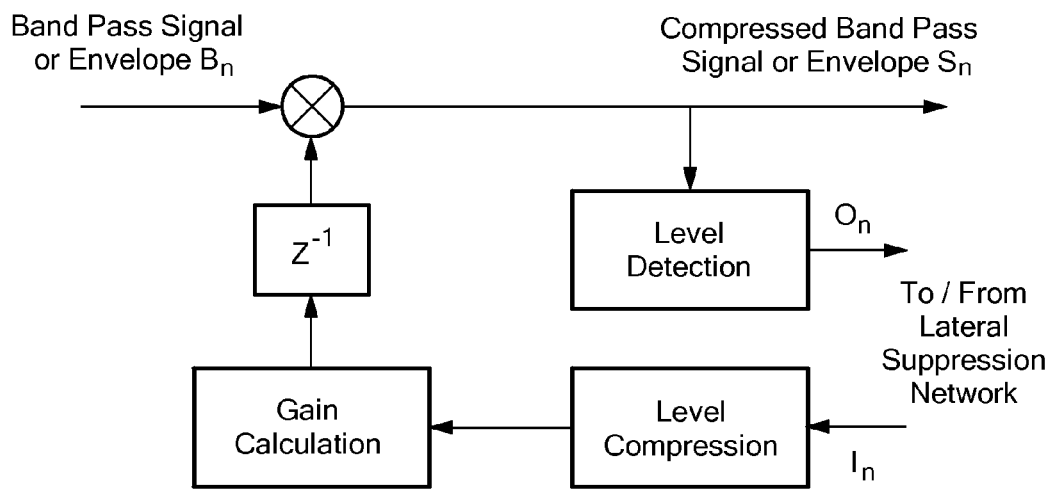
FIG. 9 shows details of an AGC arrangement with lateral suppression.

FIG. 7 shows details of the additional signal processing block which includes AGCs which are coupled with a lateral suppression network. FIG. 8 shows an example a typical implementation of an AGC having three main components: a level detector, a level compressor, and a gain calculator. Such AGCs are typically used in front end compression and could generally also be used for channel specific compression, but the existing structure does not allow for lateral suppression and spectral enhancement. FIG. 9 shows an improved arrangement that allows for interactions between AGCs where level detector signals ($O_n$) of all AGCs are routed to a lateral suppression network and the level compression stage of each AGC is fed by the output/return ($I_n$) of the network.

In a specific embodiment, the network could simply apply a matrix multiplication as given in Equation 1:

$$\vec{I} = W \cdot \vec{O} \qquad \text{Equation 1}$$

where W is the matrix, and I and R the vectors containing all level detector and return signals, respectively. The unit matrix (Equation 2) results in individually acting AGCs:

$$W = \begin{pmatrix} 1 & 0 & 0 & \ldots & \ldots & 0 & 0 & 0 \\ 0 & 1 & 0 & \ldots & \ldots & 0 & 0 & 0 \\ 0 & 0 & 1 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0 & 1 & 0 \\ 0 & 0 & 0 & \ldots & \ldots & 0 & 0 & 1 \end{pmatrix} \qquad \text{Equation 2}$$

whereas Equation 3 shows a setup of the lateral suppression network, where level detector signals of three neighboring channels are averaged:

$$W = \begin{pmatrix} 0.33 & 0.66 & 0 & \ldots & \ldots & 0 & 0 & 0 \\ 0.33 & 0.33 & 0.33 & \ldots & \ldots & 0 & 0 & 0 \\ 0 & 0 & 0 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.33 & 0.33 & 0.33 \\ 0 & 0 & 0 & \ldots & \ldots & 0 & 0.66 & 0.33 \end{pmatrix} \qquad \text{Equation 3}$$

A similar case with a subtle difference is shown in Equation 4 where elements in the main diagonal of the matrix are smaller:

$$W = \begin{pmatrix} 0.1 & 0.9 & 0 & \ldots & \ldots & 0 & 0 & 0 \\ 0.45 & 0.1 & 0.45 & \ldots & \ldots & 0 & 0 & 0 \\ 0 & 0.45 & 0.1 & \ldots & \ldots & 0 & 0 & 0 \\ \ldots & \ldots & \ldots & \ldots & \ldots & \ldots & \ldots & \ldots \\ 0 & 0 & 0 & \ldots & \ldots & 0.45 & 0.1 & 0.45 \\ 0 & 0 & 0 & \ldots & \ldots & 0 & 0.9 & 0.1 \end{pmatrix} \qquad \text{Equation 4}$$

In this case a channel containing smaller amplitude would be suppressed by a neighboring channel with higher amplitude. The main diagonal is set to zero in Equation 5:

$$W = \begin{pmatrix} 0 & 0.5 & 0.25 & \ldots & \ldots & 0.01 & 0 & 0 \\ 0.33 & 0 & 0.33 & \ldots & \ldots & 0.01 & 0.01 & 0 \\ 0.14 & 0.29 & 0 & \ldots & \ldots & 0.02 & 0.01 & 0 \\ \ldots & \ldots & \ldots & \ldots & \ldots & \ldots & \ldots & \ldots \\ 0 & 0.01 & 0.01 & \ldots & \ldots & 0.33 & 0 & 0.33 \\ 0 & 0 & 0.01 & \ldots & \ldots & 0.25 & 0.5 & 0 \end{pmatrix} \quad \text{Equation 5}$$

Additionally, all other elements decay exponentially. Decay characteristics can be different in the upper and lower triangular matrix. The system allows individual adjustment of the range and form of suppression in terms of analysis bands. Numerical stability of the system can be provided by normalization of the matrix and application-specific constraints.

Laterally suppressed AGCs (as described above) allow simulation of spectral masking and/or spectral sharpening effects as known from normal hearing. At the same time, distant channels can be configured to work independently. Thus, the negative side effects (described in the Background) of single channel AGC and simple independent channel specific AGCs can be avoided. For example, a low frequency signal (e.g. speech) will no longer be suppressed by a louder high frequency signal (e.g., noise). And bilaterally implanted users would be able to more correctly identify directions of simultaneous spectrally separated signals. Spectral smearing as seen with entirely independent AGCs can be avoided and spectral differences can be enhanced for further signal processing stages. Besides laterally suppressed AGCs as described above, a weighting matrix can be used with a similar architecture to implement independent AGCs or laterally averaged AGCs.

Embodiments of the invention may be implemented in whole or in part any conventional computer programming language. For example, preferred embodiments may be implemented in a procedural programming language (e.g., "C") or an object oriented programming language (e.g., "C++", Python). Alternative embodiments of the invention may be implemented as pre-programmed hardware elements, other related components, or as a combination of hardware and software components.

Embodiments can be implemented in whole or in part as a computer program product for use with a computer system. Such implementation may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein with respect to the system. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

Although various exemplary embodiments of the invention have been disclosed, it should be apparent to those skilled in the art that various changes and modifications can be made which will achieve some of the advantages of the invention without departing from the true scope of the invention.

What is claimed is:

1. A method of generating electrode stimulation signals for a plurality of stimulation electrodes in an implanted electrode array, the method comprising:
    processing an acoustic audio signal with a bank of filters to generate a set of band pass signals, each band pass signal corresponding to a band of audio frequencies associated with one of the filters;
    using a lateral suppression network based on automatic gain control circuitry using a multiplication matrix to perform channel specific dynamic amplitude mapping of the band pass signals to generate a set of compressed band pass signals;
    extracting stimulation information from the compressed band pass signals to generate a set of stimulation timing signals; and
    developing the stimulation timing signals into a set of electrode stimulation signals to the stimulation electrodes.

2. A method according to claim 1, wherein the lateral suppression network allows individual lateral decay of suppression.

3. A method according to claim 1, wherein matrix elements along a main diagonal have a lower value than adjacent matrix elements.

4. A method according to claim 1, wherein matrix elements along a main diagonal have a zero value.

5. A method according to claim 1, wherein the lateral suppression network weights one or more of the band pass signals to be independent of the other band pass signals.

6. A method according to claim 1, wherein the lateral suppression network weights one or more of the band pass signals to be influenced by spatially adjacent band pass signals.

7. A method according to claim 6, wherein the weighted band pass signals are averaged with the spatially adjacent band pass signals.

8. A method according to claim 6, wherein the lateral suppression network laterally suppresses the one or more band pass signals when a spatially adjacent band pass signal has a higher amplitude.

9. A cochlear implant system adapted to use the method according to any of claims 1-8.

10. A non-transitory computer readable storage medium generating electrode stimulation signals for a plurality of stimulation electrodes in an implanted electrode array, the product comprising:
    program code for processing an acoustic audio signal with a bank of filters to generate a set of band pass signals, each band pass signal corresponding to a band of audio frequencies associated with one of the filters;

program code for using a lateral suppression network based on automatic gain control circuitry using a multiplication matrix to perform channel specific dynamic amplitude mapping of the band pass signals to generate a set of compressed band pass signals;

program code for extracting stimulation information from the compressed band pass signals to generate a set of stimulation timing signals; and program code for developing the stimulation timing signals into a set of electrode stimulation signals to the stimulation electrodes.

11. A non-transitory computer readable storage medium according to claim 10, wherein the lateral suppression network allows individual lateral decay of suppression.

12. A non-transitory computer readable storage medium according to claim 10, wherein matrix elements along a main diagonal have a lower value than adjacent matrix elements.

13. A non-transitory computer readable storage medium according to claim 10, wherein matrix elements along a main diagonal have a zero value.

14. A non-transitory computer readable storage medium according to claim 10, wherein the lateral suppression network weights one or more of the band pass signals to be independent of the other band pass signals.

15. A non-transitory computer readable storage medium according to claim 10, wherein the lateral suppression network weights one or more of the band pass signals to be influenced by spatially adjacent band pass signals.

16. A non-transitory computer readable storage medium according to claim 15, wherein the weighted band pass signals are averaged with the spatially adjacent band pass signals.

17. A non-transitory computer readable storage medium according to claim 15, wherein the lateral suppression network laterally suppresses the one or more band pass signals when a spatially adjacent band pass signal has a higher amplitude.

* * * * *

UNITED STATES PATENT AND TRADEMARK OFFICE
CERTIFICATE OF CORRECTION

PATENT NO. : 8,412,343 B2
APPLICATION NO. : 12/695240
DATED : April 2, 2013
INVENTOR(S) : Peter Schleich Page 1 of 1

It is certified that error appears in the above-identified patent and that said Letters Patent is hereby corrected as shown below:

In the Claims

In Col. 6, line 62
Insert the word --for-- after "medium"

Signed and Sealed this
Second Day of July, 2013

Teresa Stanek Rea
*Acting Director of the United States Patent and Trademark Office*